(12) United States Patent
Wang et al.

(10) Patent No.: US 10,265,270 B2
(45) Date of Patent: Apr. 23, 2019

(54) SOLID DISPERSION OF DECOQUINATE, A PREPARATION PROCESS AND ITS APPLICATION

(71) Applicant: GUANGZHOU CAS LAMVAC BIOTECH CO., LTD., Guangzhou (CN)

(72) Inventors: Hongxing Wang, Guangzhou (CN); Yinzhou Fan, Guangzhou (CN); Xueqing Chen, Guangzhou (CN); Xiaoping Chen, Guangzhou (CN)

(73) Assignee: Bluelight Pharmatech Co., Ltd., Guangzhou (CN)

( * ) Notice: Subject to any disclaimer, the term of this patent is extended or adjusted under 35 U.S.C. 154(b) by 0 days.

(21) Appl. No.: 15/531,244

(22) PCT Filed: Dec. 8, 2015

(86) PCT No.: PCT/CN2015/096689
§ 371 (c)(1),
(2) Date: May 26, 2017

(87) PCT Pub. No.: WO2017/096530
PCT Pub. Date: Jun. 15, 2017

(65) Prior Publication Data
US 2017/0360708 A1 Dec. 21, 2017

(51) Int. Cl.
*A61K 9/14* (2006.01)
*A61K 31/47* (2006.01)
*A61K 47/10* (2017.01)
*A61K 47/32* (2006.01)
*A61K 47/34* (2017.01)

(52) U.S. Cl.
CPC ............. *A61K 9/146* (2013.01); *A61K 31/47* (2013.01); *A61K 47/10* (2013.01); *A61K 47/32* (2013.01); *A61K 47/34* (2013.01); *Y02A 50/411* (2018.01)

(58) Field of Classification Search
None
See application file for complete search history.

(56) References Cited

FOREIGN PATENT DOCUMENTS

| CN | 101564376 A | * 10/2009 | ............. A61K 47/38 |
| CN | 102274189 A | * 12/2011 | ............... A61K 9/14 |

* cited by examiner

*Primary Examiner* — Brian J Davis
(74) *Attorney, Agent, or Firm* — Gregory L. Porter; Hunton Andrews Kurth LLP

(57) ABSTRACT

The present invention relates to a hot melt extrusion composition, a process for preparing a hot melt extruded product using the hot melt extrusion composition, a solid dispersion of decoquinate, and pharmaceutical uses of the composition and the solid dispersion of decoquinate. The hot melt extrusion composition comprises 5 to 30% of decoquinate, 60 to 90% of a polymeric carrier and 0 to 10% of a surfactant. The hot melt extrusion composition can be melted into a liquid at a temperature below the melting point of decoquinate to achieve complete mixing, effectively avoiding the possible thermal decomposition of decoquinate and other components of the composition during the hot-melt process, thus retaining their original structures and pharmacodynamic activity. In the solid dispersion of decoquinate according to the present invention, the active pharmaceutical ingredient and the formulation excipients are melted into amorphous material with homogeneity, possessing improved solubility and drug releasing rate as well as enhanced oral bioavailability and efficacy.

12 Claims, 11 Drawing Sheets

SOLID DISPERSION OF DECOQUINATE, A PREPARATION PROCESS AND ITS APPLICATION

FIELD OF THE INVENTION

The present invention relates to the field of medical technology, and in particular, to a composition for hot-melt extrusion, a process for producing a hot-melt extruded product using the composition for hot melt extrusion, the obtained solid dispersion of decoquinate and the pharmaceutical application of the composition and the solid dispersion of decoquinate.

BACKGROUND

Malaria is a mosquito-borne infectious disease caused by the infection of *Plasmodium* via the bites of infected female *anopheles* mosquito or the transfusion of blood from patients carrying *Plasmodium* parasites. There are four *Plasmodium* species affecting humans, namely, *Plasmodium vivax, Plasmodium malariae, Plasmodium falciparum* and *Plasmodium ovale*. There is also a malaria which both human and monkey can suffer from and is caused by *Plasmodium knowlesi*. Malaria causes symptoms which mainly include intermittent attacks, fever, sweating, weakness, vomiting, and headache. As a result of long and repeated attacks, anemia and splenomegaly usually occur. Patients infected with *Plasmodium falciparum* can develop into cerebral malaria and even death if untreated. After many years of efforts made by the healthcare workers, the incidence of malaria in China has dropped to a very low level. According to the epidemiological surveillance made in 1992, the number of patients throughout the whole country fell to 70,000. In China, *Plasmodium vivax* and *Plasmodium falciparum* account for the majority of cases, while the other three are rare. In recent years, however, there are increasing cases imported from abroad or brought back by travelers to areas where the disease is common. Globally, nevertheless, malaria is still widespread in many countries and regions, and especially in some countries of Africa, Southeast Asia, Central America and South America. The mortality of severe cases caused by *Plasmodium falciparum* is extremely high. According to the statistics made by the World Health Organization (WHO) in recent years, it is estimated that there are nearly 3.4 billion people in the world at the risk of malaria transmission, of which 1.2 billion are at high risk. Malaria caused an estimated 620,000 deaths each year, of which more than 70 percent are children under 5.

Depending on the host, *Plasmodium* can be the species that infects humans and the species that infects other animals. The life cycle of *Plasmodium* infecting humans has the stage inside the human's body and the stage inside the *anopheles*' body; in the human's body there are the liver stage and the erythrocyte stage. The anti-malarial artemisinin invented by Chinese scientists and most of the classic anti-malarial medications such as chloroquine act during the erythrocyte stage but have no inhibitory effects on the parasites at the liver stage. Artemisinin is the most commonly used first line antimalarial drug. Chinese manufacturers provide 90% of the raw material of artemisinin. Three suppliers of the pharmaceutical drugs chosen by world health organization (WHO) are foreign companies for the reason that Chinese manufactories do not produce the kinds of artemisinin formulations for which there is a great demand by other countries. Resistance of *Plasmodium* to current antimalarial drugs has emerged worldwide. In addition to extensive resistance to chloroquine and sulfonamides, *Plasmodium* also exhibits drug resistance to the first-line antimalarial drug, i.e. the artemisinin component which is the core drug of the artemisinin-based combination therapy (Ariel, F. et al., A molecular marker of artemisinin-resistant *Plasmodium falciparum* malaria, Nature 505, 50-55, 2014). Primaquine is a relatively new antimalarial drug used for the liver stage. However, this drug has serious side effects. It can not only cause certain patients with malaria to suffer from acute hemolytic anemia, but also have no inhibitory effect at all on the *Plasmodium falciparum* of the blood stage, and thus it cannot be used as the medication to control the symptoms. There also exist such liver stage medications as Malarone consisting of atovaquone/proguanil combination. However, the drug is costly for the majority of malaria patients. Thus, the global market needs new, efficient and affordable anti-malarial drugs with low toxicity and no drug resistance to protect susceptible populations.

Decoquinate (CAS No. 18507-89-6) is a coccidiostatic drug used mainly in poultry and livestock such as cattle, horses and sheep. It is used widely in many countries of the world including China. It acts mainly in the gut to suppress the coccidia infection. In recent years, it has been found that decoquinate (DQ) has a potent inhibitory and killing effect against *Plasmodium* both in vitro and in vivo (Science 2011; 334: 1372-7). With respect to the anti-malarial efficacy, it has obvious advantages over the existing anti-malarial drugs (JID 2012: 205: 1278-86). It acts by inhibiting the cytochrome bc1 complex of *Plasmodium mitochondria*. DQ has both inhibitory effects on the development of *Plasmodium* during the liver stage and on the reproduction of *Plasmodium* during the erythrocyte stage. Whether it is used as a veterinary medicine or as a testing article in animal toxicology studies, DQ has not been found to have any significant side effects and toxicity. Studies conducted by the present inventors and other investigators have shown that DQ does not have resistance from chloroquine-resistant *Plasmodium* (for references: a DQ nano-formulation and its preparation and use; JID 2012: 205: 1278-86). In addition, some studies demonstrated that DQ had killing effects on neurotoxin *Sarcocystis* (*Intern J Appl Res Vet Med*. Vol. 10, No. 1, 2012) and *Toxoplasma gondii* (Veterinary Record, 1996 [138] 434-436).

Decoquinate with a molecular weight of 417.54, low water solubility, and high lipophilicity (log Kow value of 5.2-5.5) can be obtained by chemical synthesis. DQ is poorly absorbed by the intestine due to its water insolubility. When used as a veterinary drug against coccidiosis, it does not need to be absorbed by the intestine into the body to exert a pharmacological effect. However, the oral dosage form is still the most convenient and feasible way for administration, and therefore, in order to develop DQ as an oral form of antimalarial drugs, it is essential to solve the solubility problem for effective absorption by the intestine.

For insoluble compounds with high biological activity in vitro, methods such as making it into salt, enhancing its solubility, and reducing its particle size can be used to increase the intestinal absorption and bioavailability of the drug. A variety of attempts to make DQ into a salt to enhance its water-solubility has failed. Formulation prepared by the addition of surfactants or the reduction of particle size can increase the delivery of DQ in vivo as well as anti-malarial efficacy. However, this type of methods typically requires an organic solvent, involves multiple processes, and takes a longer period of time for subsequent manufacturing process. The preparation of a solid dispersion of DQ by hot-melt only method can solve the problem of its water insolubility to a certain extent; however, with using this sole hot-melt method, the process is cumbersome and DQ is vulnerable to thermal decomposition and cannot be easily processed into a pharmaceutical drug, and thus it is only used to manufacture DQ as a veterinary medicine.

Solid dispersion is a commonly used formulation method in which poorly soluble or water-insoluble drug molecules, including colloidal, microcrystalline or amorphous material, are uniformly dispersed in other water-soluble materials prior to the addition of water. Hot melt extrusion (HME) method is a relatively new technology developed in the field of pharmaceutical formulation in recent years in part to solve the problem of insoluble compounds. This technology takes the advantage of combination of both solid dispersion technology and mechanical preparation process. Through the process of heating at elevated controlled temperature and pressure, twin screw rotation and flow through the die, raw materials fed through a hopper are pumped through a heated barrel, mixed, sheared, melted and extruded into a product of uniform shape and density, resulting in amorphous solid dispersions. This method does not require organic solvent and can be continuously performed at a small scale or large-scale, and therefore it is not only suitable for research and development, but also for commercial production. However, heat-labile drugs or polymer carriers are not suitable for being processed using hot melt or HME method because the decomposition of drugs or excipients and the generation of related substances will reduce the efficacy and safety profile of drugs, which therefore is the main reason for avoiding the use of HME method.

SUMMARY OF THE INVENTION

The objective of the present invention is to provide a composition for hot-melt extrusion, a process for producing a hot-melt extruded product using the composition for hot-melt extrusion, the resulted solid dispersion of decoquinate, and the pharmaceutical applications of the compositions and the solid dispersion of decoquinate.

The present invention achieves the above objective by means of the following technical solutions:

In the first aspect, the present invention provides a composition for HME, characterized in that the composition comprises, by weight percent:

5% to 30% of decoquinate;
60% to 90% of a polymeric carrier material; and
0% to 10% of a surfactant.

In a preferred embodiment, the polymeric carrier material is polyvinyl caprolactam-polyvinyl acetate-polyethylene glycol graft copolymer, copovidone, povidone or polyethylene glycol, or a combination of two or more thereof.

In a further preferred embodiment, said polyvinyl caprolactam-polyvinyl acetate-polyethylene glycol graft copolymer refers to Soluplus; Soluplus is used herein for making solid solution as well as for enhancing the solubility.

In a further preferred embodiment, the copovidone is Kollidon VA 64; and Kollidon VA 64 has a wetting property, enhances drug loading and facilitates the redissolution of solid dispersion.

In a further preferred embodiment, the povidone is povidone k17, povidone k25, povidone k30, or polyvinylpyrrolidone-10; the povidone has a wetting effect and contributes to solubilization and redissolution of the solid dispersion.

In a further preferred embodiment, said polyethylene glycol is polyethylene glycol 8000, polyethylene glycol 6000 or polyethylene glycol 4000; the polyethylene glycol mainly plays a role in reducing the melting temperature in the melting process, thereby reducing the possibility of degradation of the active ingredient decoquinate, making the formula easy processing; however, it may result in the reduction in the physical stability of the formula. In addition, polyethylene glycol can also prolong the circulation of the active ingredient decoquinate in the blood stream, increase the circulation half-life and thus help improve the efficacy.

In a preferred embodiment, the surfactant is any one of sodium lauryl sulfate, polyethylene glycol glyceryl laurate, polyethylene glycol glyceryl stearate, or polyoxyethylene hydrogenated castor oil, or a combination of two or more thereof; the surfactant is a formulation excipient for enhancing the water solubility of the poorly soluble compound such that the active ingredient decoquinate is dispersed therein in the state of a molecule or a very fine particle, thereby facilitating the enhancement of the water solubility of decoquinate.

Further preferably, the polyethylene glycol glyceryl laurate is Gelucire 44/14;

Further preferably, the polyethylene glycol glyceryl stearate is Gelucire 50/13;

Further preferably, the polyoxyethylene hydrogenated castor oil is Kolliphor RH 40; the Kolliphor RH 40 may serve to adjust the melting temperature range appropriately during the melting process of the composition, to promote inter-component cohesion of the formulation and to reduce the possibility of decomposition of the active ingredient decoquinate, thereby facilitating the formation of a solid dispersion of decoquinate with uniform density.

In addition, the polymer material used in the present invention may possess the characteristics of having the thermoplastic behavior, the ability of change in shape in the molten state, high thermal stability, no toxicity and the role of solubility enhancement. The selected surfactants in the present invention are acceptable excipients for HME approved by CFDA, FDA and other authorities and have no potential health hazards for clinical use as pharmaceutical ingredients.

In a second aspect, the present invention provides a preparation process for the solid dispersion of decoquinate comprising hot melt extruding a composition as described in the first aspect at a hot melt temperature.

In a particular embodiment, the hot melt extrusion (HME) is carried out in a hot melt extruder; in particular, the composition as described in the first aspect is mixed homogeneously, and then fed to a Twin-Screw Extruder, in which the composition is processed in the segmented screws and barrels of the machine with preset temperatures in each segment, pumped through by twin screw extrusion, and processed by die molding; the extruded material is allowed to cool down automatically at room temperature and comes out as stripped or other shapes of solid mixture, depending on the die. The stripped solid mixture is cut and pulverized to obtain powdered solid dispersion of decoquinate.

In a preferred embodiment, the temperature of hot melt extrusion is 50-200° C., preferably 120-200° C.; preferably, the screw rotation speed of the hot melt extruder is 15-300 rpm, more preferably 20to 150 rpm.

In the preparation of the solid dispersion of decoquinate, it is necessary to adjust the melting temperature in accordance with the composition of the raw materials so that the active ingredient decoquinate is effectively mixed with the polymeric carrier material as an excipient at the molecular level, but also thermal decomposition of decoquinate and excipients is avoided.

It is well known that a solid material can have crystal and non-crystal forms, and the temperature at which the crystal begins to melt is called melting point. The melting point is the temperature at which a solid changes its state from solid state to liquid state (melting). It can be generally expressed as Tm. Organic compounds generally have a fixed melting point; that is, under a certain pressure, changes between solid phase and liquid phase are very sensitive. The melting point range of a pure substance from solid to liquid is generally narrow. However, if the organic compound is mixed with other substances, the melting point will be decreased and the melting point range increased. The melting point of decoquinate is 242 to 246° C. The present invention designs a composition for hot melt extrusion comprising decoquinate in a specific composition such that when decoquinate is mixed molten with excipients such as a polymeric carrier material, a surfactant and the like, it can become liquid at a temperature lower than its own melting point, which in turn reduces the possibility of its thermal decomposition, and thus is in favor of retaining its original structure and pharmacological potency.

In a third aspect, the present invention provides a solid dispersion of decoquinate, which is prepared from the preparation process as described in the second aspect.

As described above, during the preparation of the solid dispersion of decoquinate of the present invention, the chemical structure of the active ingredient decoquinate is not changed in any way, so that its pharmacological activity is not lost; the prepared solid dispersion of decoquinate is easily suspended in the aqueous phase and is homogeneous in the aqueous phase and does not undergo any precipitation within one week; furthermore, for the solid dispersion of decoquinate of the present invention, the release rate and the dissolution of decoquinate are significantly improved, and bioavailability and antimalarial effect in animal studies are also significantly increased.

In a fourth aspect, the present invention provides an application of the composition as described in the first aspect or the solid dispersion of decoquinate as described in the third aspect in the preparation of a pharmaceutical formulation for prevention and/or treatment of a disease caused by *Plasmodium parasites;*

Preferably, said disease refers to one or more of the following malaria caused by *Plasmodium vivax, Plasmodium falciparum, Plasmodium quartan, Plasmodium ovale* and *Plasmodium knowlesi.*

The solid dispersion of decoquinate can be prepared into oral dosage forms such as tablets, granules and filled capsules, if desired.

The hot melt extrusion technique employed in the present invention is a technique for making amorphous solid dispersions, wherein decoquinate is melted or dissolved within a dispersion carrier and mixed to produce and stabilize the amorphous form of decoquinate; compared with the hot-melt only method, hot-melt extrusion technology has the advantage of mechanical process, the mixing is highly effective, and the active ingredient and all formulation components are free of thermal decomposition; and there is no need for using organic solvents throughout the process, thus reducing environmental pollution and simplifying the process.

Decoquinate, dispersed in such a solid form, can be considered as a solid solution or dispersion. Functional excipients, such as surfactants, binders, etc. are also added to the mixture to further aid in processability or to improve the dissolution performance of the formulation upon administration. Improved dissolution efficiency enhances intestinal absorption and increases bioavailability and in vivo biological activity of the pharmaceutical drug. The melt is extruded through a shape-forming outlet, and upon rapid cooling, remains a solid, single phase, glassy amorphous matrix that is shelf-stable. At the same time, post extrusion processing equipment can be adapted to manage the extruded shape, making it amendable to downstream processing into a dosage form. In general, these extruded materials are grinded to reduce the particle size so that they can be incorporated into traditional oral solid dosage forms such as tablets or capsules, while maintaining the desired release profile for the drug.

The present invention adopts the hot-melt extrusion technology to prepare the solid dispersion of decoquinate. The inventors select particular formulation excipients and a particular ratio of active component and the excipients so that when decoquinate is mixed molten with excipients such as polymeric carrier material, surfactant and the like, it can become liquid at a temperature lower than its own melting point, which greatly reduces the possibility of its thermal decomposition, and is in favor of retaining its original structure and potency; further, by optimizing the mechanical parameters, the active compound decoquinate and hot melt excipients are efficiently melted, the extruded product is uniformly produced, and thereby the process according to the present invention is superior to organic solvent method in enhancing oral bioavailability and potency of decoquinate; and compared with the related products prepared by the organic solvent method and the hot-melt method, the preparation process of the present invention is more likely to improve the production efficiency, and thus makes it easier to apply the laboratory achievements to the pilot scale test and to the industrialization level and further to the clinical application.

DETAILED DESCRIPTION

In order to facilitate understanding of the present invention, embodiments of the present invention are described as follows. It should be understood by those skilled in the art that the examples are merely illustrative of the present invention and should not be regarded as limiting the invention thereto in any way.

The materials used in the following examples and their sources

Decoquinate (batch number: 130802, molecular weight: 417.53; Zhejiang Genebest Pharmaceutical Co., Ltd.);

Loratadine standard (batch number: 100615-201404, content of 99.7%, National Institute for Food and Drug Control);

Polyvinyl caprolactam-polyvinyl acetate-polyethylene glycol graft copolymer, Product name: Soluplus, a new polymer designed for solid solutions (BASF, Germany);

Polyethylene glycol glyceryl laurate, Product name: Gelucire 44/14 (GATTEFOSSE, France);

Polyethylene glycol glyceryl stearate, Product name: Gelucire 50/13 (GATTEFOSSE, France);

Polyvinylpyrrolidone 10 (PVP10, molecular weight: 10,000, Sigma-Aldrich, USA);

Copovidone Kollidon VA 64, povidone k17, povidone k25, or povidone k30 (BASF, Germany);

Polyoxyl 40 hydrogenated castor oil, Product name: Kolliphor RH 40 (BASF, Germany);

Polyethylene glycols (PEG), Product name: PEG 8000, PEG 6000 or PEG 2000 (Sigma-Aldrich, USA);

Sodium dodecyl sulfonate (SDS, Sigma-Aldrich, USA).

EXAMPLE 1

In this example, a solid dispersion of DQ was prepared by a HME method from a composition for HME comprising DQ as an active ingredient, Soluplus, Kollidon VA 64 and PEG 6000. The composition for HME comprised, by percentage of the total composition weight, 10% of DQ, 53% of Soluplus, 27% of Kollidon VA 64 and 10% of PEG 6000. The specific preparation procedure was as follows:

| | |
|---|---|
| Decoquinate | 3 g |
| Soluplus | 16 g |
| Kollidon VA 64 | 8 g |
| PEG 6000 | 3 g |

The above weighed materials were blended to homogeneity. The melting temperature of the twin-screw hot-melt extruder was set to 120-160° C. When all the actual temperatures reached the set temperature, the blended were added, the screw initiated slowly with a start speed of 20 rpm, and then depending on the pressure and torque figures on the machine display, if the figures were displayed within the normal range, the screw speed was turned up to 150 rpm. The feeding materials underwent heating at different segments of barrel, mixing, melting, and being pushed by extrusion, and then the melted materials extruded from the die in a stripped shape were instantly cooled to a solid at room temperature, which was then pulverized to obtain a powdered solid dispersion of DQ.

Figure 1:
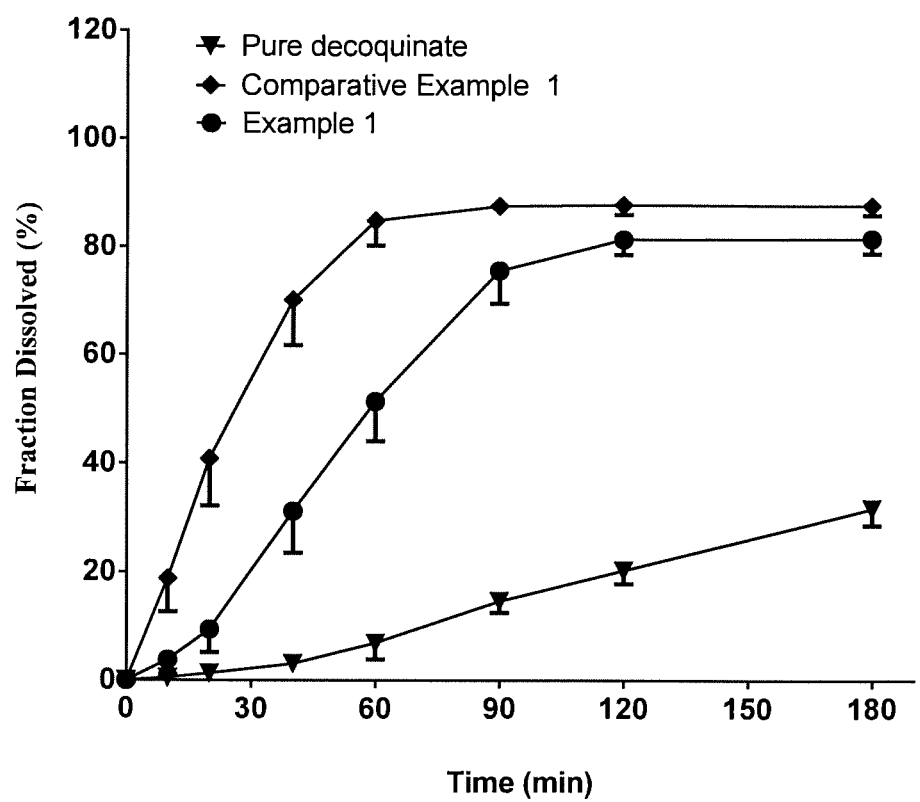
FIG. 1 illustrates a comparison of the in vitro dissolution rate of the solid dispersion of decoquinate (DQ) prepared in Example 1 with that of DQ prepared in Comparative Example 1 and pure DQ.

The solid dispersion of DQ prepared in the present example had a uniformed matrix and was homogeneously suspended in aqueous phase. The average particle size measured for the above suspended DQ was from 2 to 5 microns; the cumulative dissolution percentage was over 75% in 90 minutes (FIG. 1).

EXAMPLE 2

In this example, a solid dispersion of DQ was prepared by a HME method from a composition for HME comprising DQ as an active ingredient, Soluplus, Kollidon VA 64 and SDS. The composition for HME comprised, by percentage of the total composition weight, 10% of DQ, 65% of Soluplus, 15% of Kollidon VA 64, and 10% of SDS. The specific preparation procedure was as follows:

| | |
|---|---|
| Decoquinate | 2 g |
| Soluplus | 13 g |
| Kollidon VA 64 | 3 g |
| SDS | 2 g |

The above weighed materials were blended to homogeneity. The parameter settings for the hot-melt extruder and the operation procedures after feeding the blended material were the same as those of Example 1.

Figure 2:
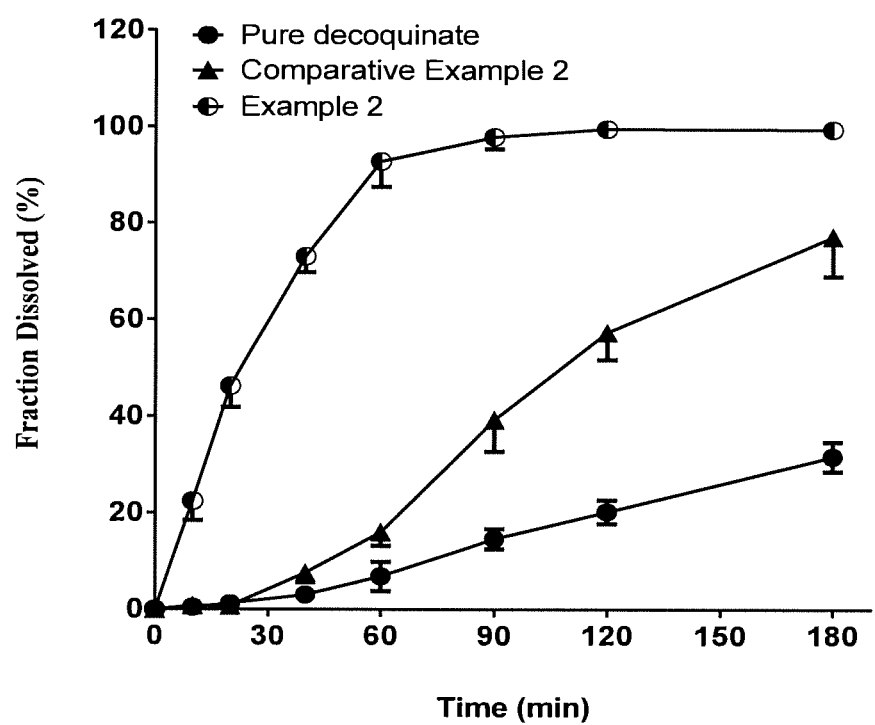
FIG. 2 illustrates a comparison of the in vitro dissolution rate of the solid dispersion of DQ prepared in Example 2 with that of DQ prepared in Comparative Example 2 and the pure DQ.

The solid dispersion of DQ prepared in the present example had a uniformed matrix and was homogeneously suspended in aqueous phase. The average particle size measured for the above suspended DQ was from 2 to 5 microns; the cumulative dissolution percentage was over 75% in 90 minutes (FIG. 2).

EXAMPLE 3

In this example, a solid dispersion of DQ was prepared by a HME method from a composition for HME comprising DQ as an active ingredient, Kollidon VA 64 and Soluplus. The composition for HME comprised, by percentage of the total composition weight, 20% of DQ, 62.33% of Soluplus, and 17.66% of Kollidon VA 64. The specific preparation procedure was as follows:

| | |
|---|---|
| Decoquinate | 6.0 g |
| Soluplus | 18.7 g |
| Kollidon VA 64 | 5.3 g |

The above weighed materials were blended to homogeneity. The parameter settings for the hot-melt extruder and the operation procedures after feeding the blended material were the same as those of Example 1.

Figure 3:
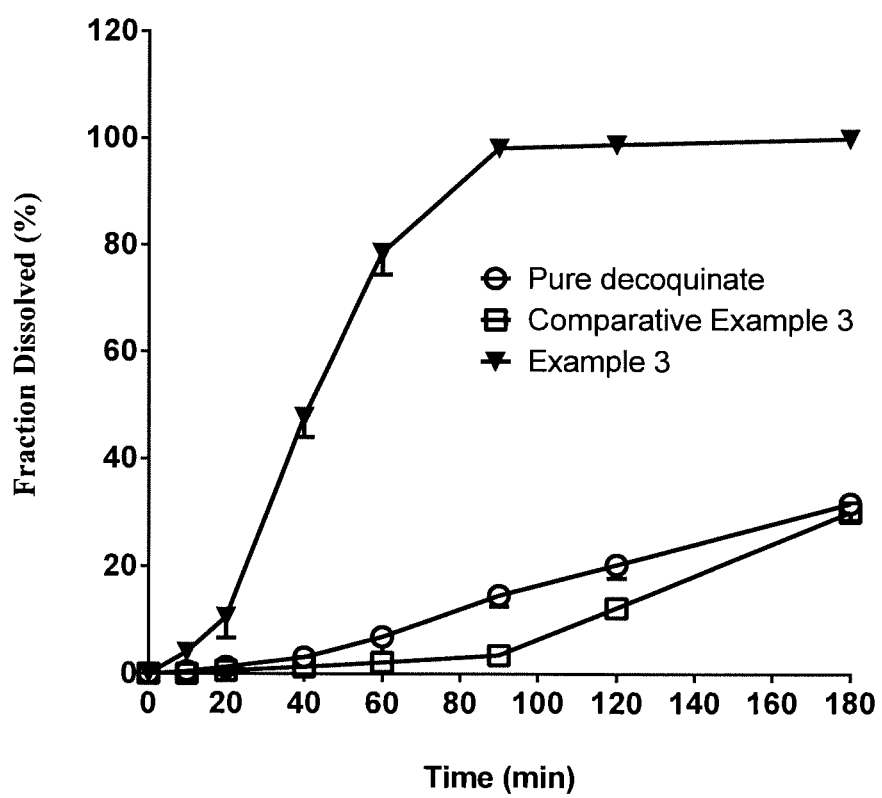
FIG. 3 illustrates a comparison of the in vitro dissolution rate of the solid dispersion of DQ prepared in Example 3 with that of DQ prepared in Comparative Example 3 and the pure DQ.
Figure 11:
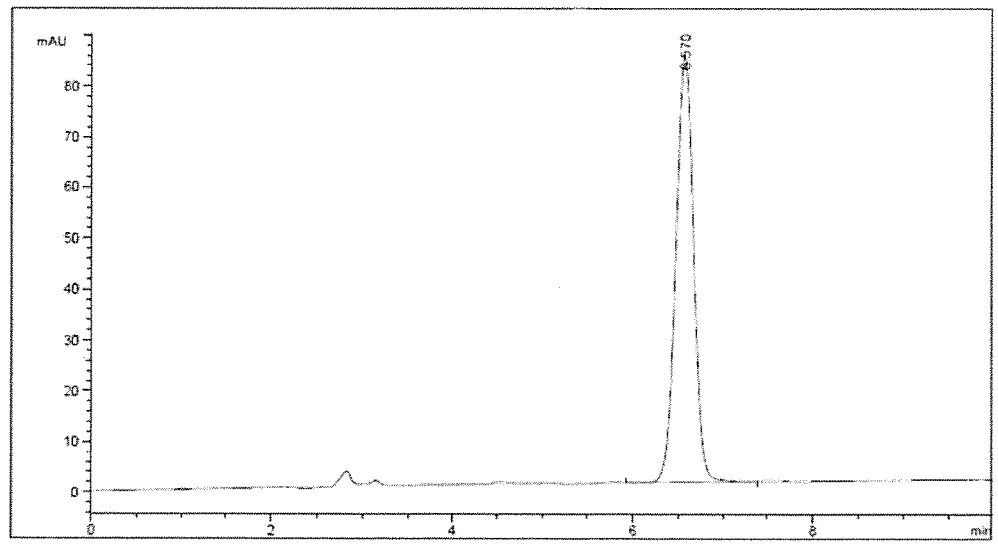
FIG. 11 is a HPLC analysis graph of pure DQ (used as a standard).
Figure 13:
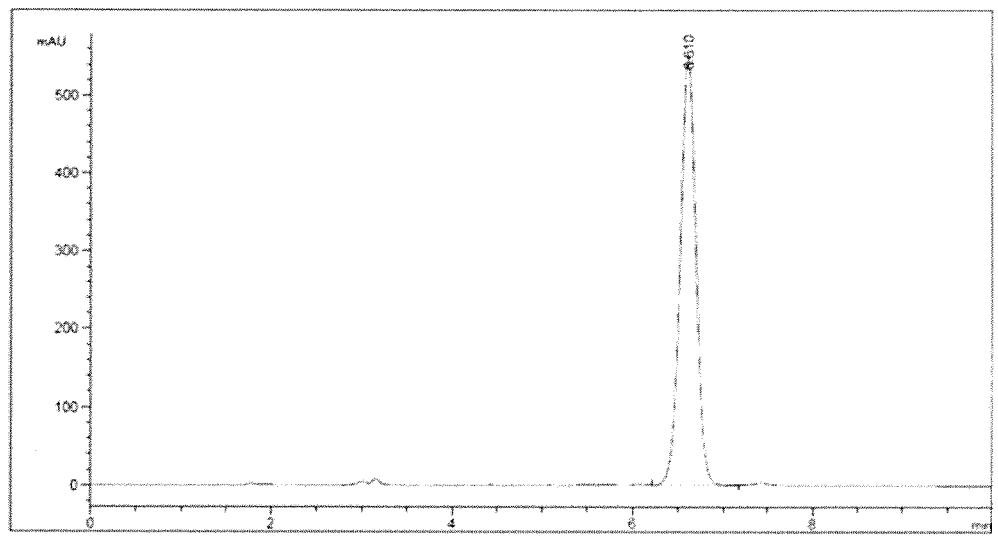
FIG. 13 is a HPLC analysis graph of DQ in the solid dispersion of DQ prepared by the hot melt extrusion (HME) technique in Example 3; this figure shows that, after preparation by the HME technique, there is no change in either the peak pattern or the retention time of DQ in the HPLC analysis.

The solid dispersion of DQ prepared in the present example had a uniformed matrix and was homogeneously suspended in aqueous phase. HPLC analysis showed no change in the retention time and content of the active ingredient DQ in the product (FIG. 13) compared with the DQ standard (FIG. 11). The average particle size measured for the above suspended DQ was from 2 to 5 microns; the cumulative dissolution percentage was over 95% in 90 minutes (FIG. 3).

EXAMPLE 4

In this example, a solid dispersion of DQ was prepared by a HME method from a composition for HME comprising DQ as an active ingredient, Soluplus and Kollidon VA 64. The composition for HME comprised, by percentage of the total composition weight, 20% of DQ, 53% of Soluplus, and 27% of Kollidon VA 64. The specific preparation procedure was as follows:

| | |
|---|---|
| Decoquinate | 6.0 g |
| Soluplus | 16.0 g |
| Kollidon VA 64 | 8.0 g |

The above weighed materials were blended to homogeneity. The parameter settings for the hot-melt extruder and the operation procedures after feeding the blended material were the same as those of Example 1.

Figure 4:
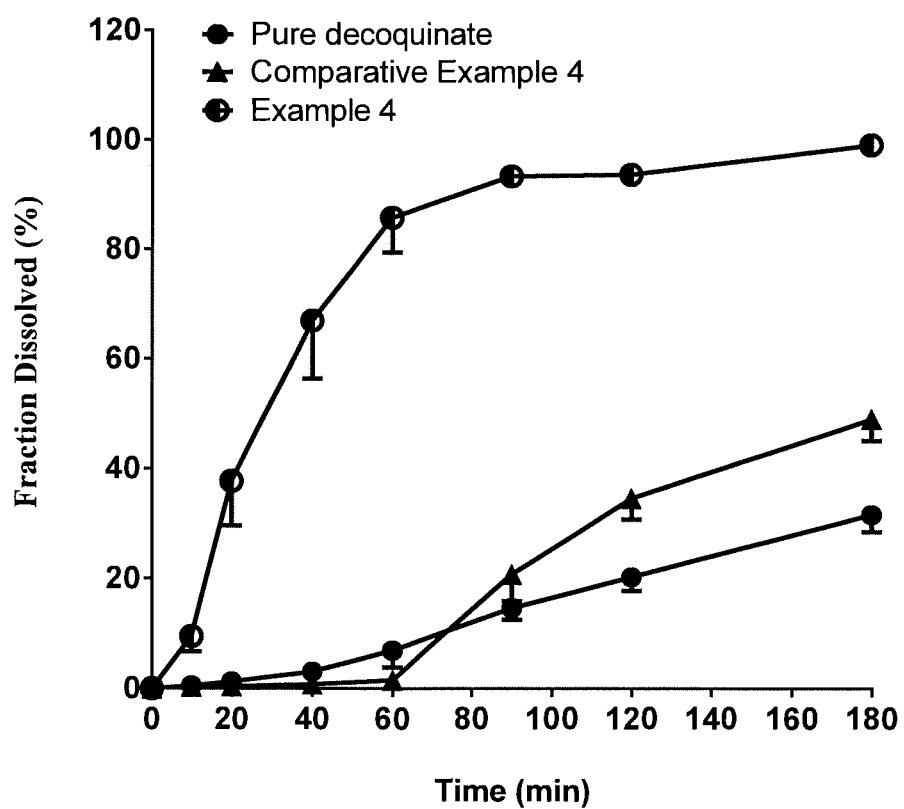
FIG. 4 illustrates a comparison of the in vitro dissolution rate of the solid dispersion of DQ prepared in Example 4 with that of DQ prepared in Comparative Example 4 and the pure DQ.

The solid dispersion of DQ prepared in the present example had a uniformed matrix and was homogeneously suspended in aqueous phase. The average particle size measured for the suspended DQ was from 2 to 5 microns; the cumulative dissolution percentage was over 90% in 90 minutes (FIG. 4).

EXAMPLE 5

In this example, a solid dispersion of DQ was prepared by a HME method from a composition for HME comprising DQ as an active ingredient and povidone PVP10. The composition for HME comprised, by percentage of the total composition weight, 10% of DQ and 90% of PVP10. The specific preparation procedure was as follows:

| | |
|---|---|
| Decoquinate | 2.0 g |
| PVP 10 | 18.0 g |

The above weighed materials were blended to homogeneity. The parameter settings for the hot-melt extruder and the operation procedures after feeding the blended material were the same as those of Example 1.

Figure 5:
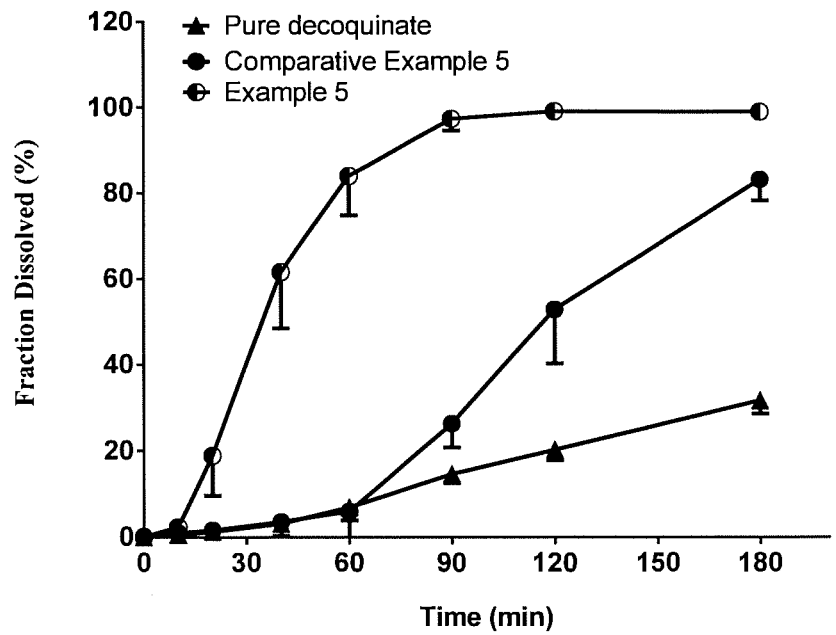
FIG. 5 illustrates a comparison of the in vitro dissolution rate of the solid dispersion of DQ prepared in Example 5 with that of DQ prepared in Comparative Example 5 and the pure DQ.

The particle size measurement showed that the average particle size was between 2 and 5 microns; the cumulative dissolution percentage was over 95% in 90 minutes (FIG. 5).

EXAMPLE 6

In this example, a solid dispersion of DQ was prepared by a HME method from a composition for HME comprising DQ as an active ingredient, Soluplus, Kollidon VA 64 and PEG 6000. The composition for HME comprised, by percentage of the total composition weight, 15% of Soluplus, 65% of Kollidon VA 64, and 10% of PEG 6000. The specific preparation procedure was as follows:

| | |
|---|---|
| Decoquinate | 2.0 g |
| PEG 6000 | 2.0 g |
| Soluplus | 3.0 g |
| Kollidon VA 64 | 13.0 g |

The above weighed materials were blended to homogeneity. The parameter settings for the hot-melt extruder and the operation procedures after feeding the blended material were the same as those of Example 1.

Figure 6:
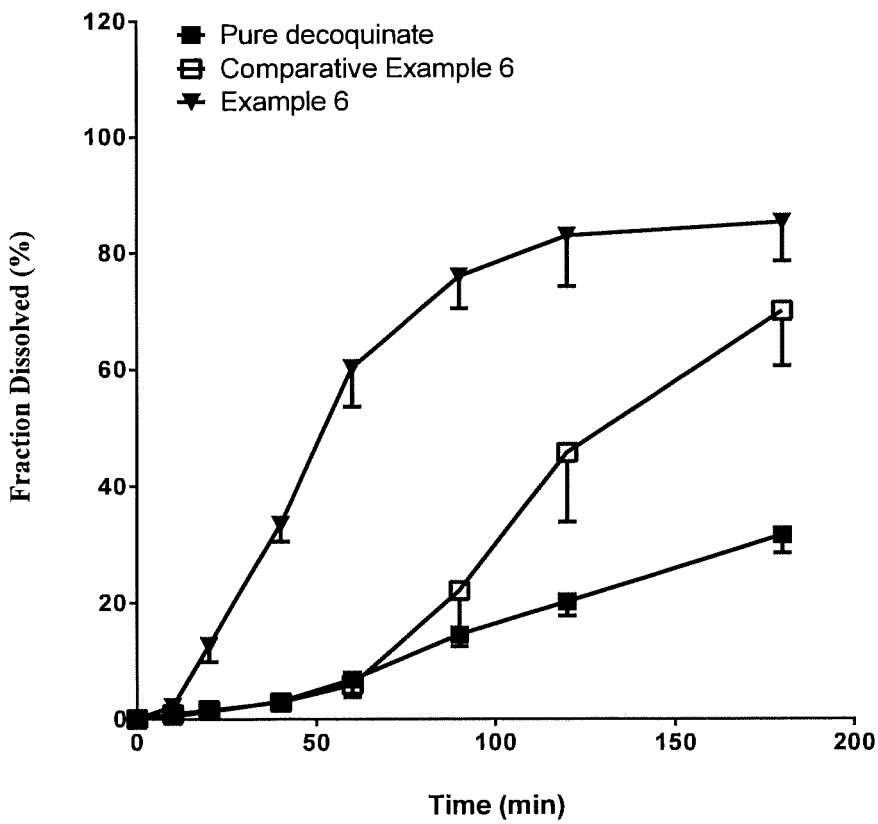
FIG. 6 illustrates a comparison of the in vitro dissolution rate of the solid dispersion of DQ prepared in Example 6 with that of DQ prepared in Comparative Example 6 and the pure DQ.

The solid dispersion of decoquinate prepared in the present example had a uniformed matrix and was homogeneously suspended in aqueous phase. The average particle size measured for the suspended DQ was from 2 to 5 microns; the cumulative dissolution percentage was over 75% in 90 minutes (FIG. 6).

EXAMPLE 7

In this example, a solid dispersion of DQ was prepared by a HME method from a composition for HME comprising DQ as an active ingredient, Soluplus and Kollidon VA 64. The composition for HME comprised, by percentage of the total composition weight, 10% of DQ, 60% of Soluplus, and 30% of Kollidon VA 64. The specific preparation procedure was as follows:

| | |
|---|---|
| Decoquinate | 3.0 g |
| Soluplus | 18.0 g |
| Kollidon VA 64 | 9.0 g |

The above weighed materials were blended to homogeneity. The parameter settings for the hot-melt extruder and the operation procedures after feeding the blended material were the same as those of Example 1.

Figure 7:
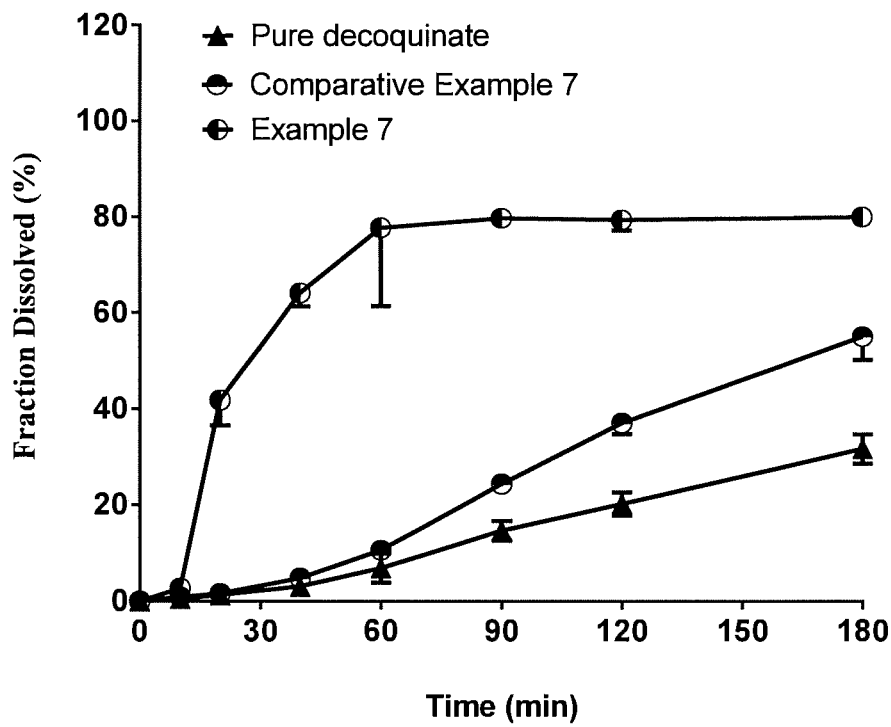
FIG. 7 illustrates a comparison of the in vitro dissolution rate of the solid dispersion of DQ prepared in Example 7 with that of DQ prepared in Comparative Example 7 and the pure DQ.

The solid dispersion of DQ prepared in the present example had a uniformed matrix and was homogeneously suspended in aqueous phase. The average particle size measured for the suspended DQ was from 2 to 5 microns; the cumulative dissolution percentage was over 75% in 60 minutes (FIG. 7).

EXAMPLE 8

In this example, a solid dispersion of DQ was prepared by a HME method from a composition for HME comprising DQ as an active ingredient, Soluplus and Kollidon VA 64. The composition for HME comprised, by percentage of the total composition weight, 20% of DQ, 71% of Soluplus, and 9% of Kollidon VA 64. The specific preparation procedure was as follows:

| Decoquinate | 6.0 g |
|---|---|
| Soluplus | 21.3 g |
| Kollidon VA 64 | 2.7 g |

The above weighed materials were blended to homogeneity. The parameter settings for the hot-melt extruder and the operation procedures after feeding the blended were the same as those of Example 1.

Figure 8:
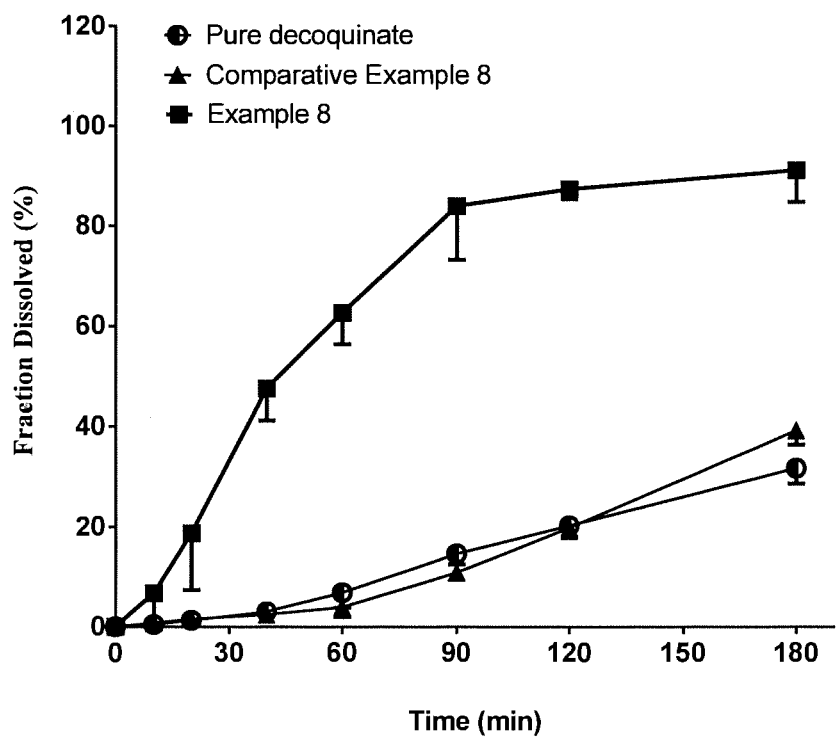
FIG. 8 illustrates a comparison of the in vitro dissolution rate of the solid dispersion of DQ prepared in Example 8 with that of DQ prepared in Comparative Example 8 and the pure DQ.

The solid dispersion of DQ prepared in the present example had a uniformed matrix and was homogeneously suspended in aqueous phase. The average particle size measured for the suspended DQ was from 2 to 5 microns; the cumulative dissolution percentage was over 80% in 90 minutes (FIG. 8).

The inventors carried out high pressure liquid chromatography (HPLC) analysis and differential scanning calorimetry (DSC) analysis of the products of the above examples (the specific analysis methods are described below). HPLC analysis showed no change in retention time and content of the active ingredient, DQ, in the products of all examples compared to the DQ standard (FIG. 11), consistent with the HPLC analysis of Example 1 (FIG. 9B). The DSC analysis showed that DQ, the active ingredient of the products in all examples, had been dispersed in the formulation excipients through melting process compared to the DQ standard.

COMPARATIVE EXAMPLE 1

In this comparative example, a solid dispersion of DQ was prepared by a HME method from a composition for HME comprising DQ as an active ingredient, Soluplus and Kollidon VA 64. The composition for HME comprised, by percentage of the total composition weight, 60% of Soluplus, and 30% of Kollidon VA 64. The specific preparation procedure was as follows:

| Decoquinate | 3 g |
|---|---|
| Soluplus | 18 g |
| Kollidon VA 64 | 9 g |

The above weighed materials were blended to homogeneity. The parameter settings for the hot-melt extruder and the operation procedures after feeding the blended material were the same as those of Example 1.

The solid dispersion of DQ prepared in the present example had a uniformed matrix and was homogeneously suspended in aqueous phase. HPLC analysis showed no change in the retention time and content of the active ingredient DQ in the product, as compared with the DQ standard. The average particle size measured for the suspended DQ was from 2 to 5 microns; the cumulative dissolution percentage was over 80% in 60 minutes (FIG. 1).

COMPARATIVE EXAMPLE 2

In this comparative example, a solid dispersion of DQ was prepared by a HME method from a composition for HME comprising DQ as an active ingredient, Soluplus and Kollidon VA 64. The composition for HME comprised, by percentage of the total composition weight, 10% of DQ, 70% of Soluplus, and 20% of Kollidon VA 64. The specific preparation procedure was as follows:

| Decoquinate | 2 g |
|---|---|
| Soluplus | 14 g |
| Kollidon VA 64 | 4 g |

The above weighed materials were blended to homogeneity. The parameter settings for the hot-melt extruder and the operation procedures after feeding the blended were the same as those of Example 1.

The solid dispersion of DQ prepared in the present example had a uniformed matrix and was homogeneously suspended in aqueous phase. HPLC analysis showed no change in the retention time and content of the active ingredient DQ in the product, as compared with the DQ standard. The average particle size measured for the suspended DQ was from 2 to 5 microns; the cumulative dissolution percentage was below 20% in 60 minutes (FIG. 2).

COMPARATIVE EXAMPLE 3

In this comparative example, a solid dispersion of DQ was prepared by a hot melt method from a composition comprising DQ as an active ingredient, Soluplus and Kollidon VA 64. The composition for HME comprised, by percentage of the total composition weight, 20% of DQ, 62.33% of Soluplus, and 17.66% of Kollidon VA 64. The specific preparation procedure is as follows:

| Decoquinate | 0.6 g |
|---|---|
| Soluplus | 18.7 g |
| Kollidon VA 64 | 0.53 g |

Figure 12:
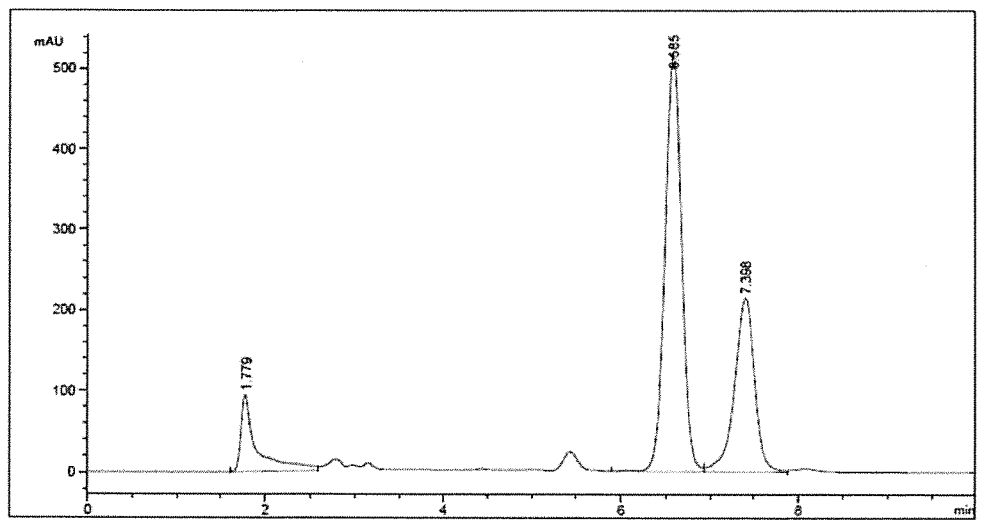
FIG. 12 is a HPLC analysis graph of DQ in the solid dispersion of DQ prepared by the hot melt method in Comparative Example 3; this figure shows that, after preparation by the hot melt only method, the peak pattern of DQ in the HPLC graph has undergone significant changes.

The above weighed materials were fully mixed. The mixture was melted at 160° C. for 3 min under stirring, and then cooled at room temperature. HPLC analysis showed that the peak shape of DQ in the solid dispersion of DQ prepared in this comparative example was altered compared to the DQ standard (FIG. 12), indicating that this preparation process can cause the active ingredient DQ to be thermally decomposed to a certain extent; the cumulative dissolution percentage of the solid dispersion of DQ was less than 20% in 60 minutes (FIG. 3).

COMPARATIVE EXAMPLE 4

In this comparative example, a solid dispersion of DQ was prepared by a hot melt method from a composition comprising DQ as an active ingredient, Soluplus and Kollidon VA 64. The composition for HME comprised, by percentage of the total composition weight, 20% of DQ, 53% of Soluplus, and 27% of Kollidon VA 64. The specific preparation procedure was as follows:

| Decoquinate | 0.6 g |
|---|---|
| Soluplus | 1.6 g |
| Kollidon VA 64 | 0.8 g |

The above weighed materials were fully mixed. The mixture was melted at 160° C. for 3 min under stirring, and then cooled at room temperature.

The cumulative dissolution percentage of the solid dispersion of DQ prepared in this comparative example was less than 20% in 60 minutes (FIG. 4).

COMPARATIVE EXAMPLE 5

In this comparative example, a solid dispersion of DQ was prepared by a HME method from a composition for HME comprising DQ as an active ingredient and Soluplus. The composition for HME comprised, by percentage of the total composition weight, 10% of DQ and 90% of Soluplus. The specific preparation procedure was as follows:

| Decoquinate | 2 g |
|---|---|
| Soluplus | 18 g |

The above weighed materials were blended to homogeneity. The parameter settings for the hot-melt extruder and the operation procedures after feeding the blended were the same as those of Example 1.

HPLC analysis showed that neither the retention time nor the content of DQ in the product was changed compared with the DQ standard; the particle size measurement showed that the average particle size of the DQ was 2-5 microns; the cumulative dissolution percentage was less than 20% within 60 min (FIG. 5).

COMPARATIVE EXAMPLE 6

In this comparative example, a solid dispersion of DQ was prepared by a HME method from a composition for HME comprising DQ as an active ingredient, Soluplus and copovidone Kollidon VA 64. The composition for HME comprised, by percentage of the total composition weight, 10% of DQ, 20% of Soluplus, and 70% of Kollidon VA 64. The specific preparation procedure was as follows:

| Decoquinate | 2 g |
|---|---|
| Soluplus | 4 g |
| Kollidon VA 64 | 14 g |

The above weighed materials were blended to homogeneity. The parameter settings for the hot-melt extruder and the operation procedures after feeding the blended were the same as those of Example 1.

The solid dispersion of DQ prepared in the present example had a uniformed matrix and was homogeneously suspended in aqueous phase. HPLC analysis showed that neither the retention time nor the content of DQ in the product was changed compared with the DQ standard; the particle size measurement showed that the average particle size of the DQ was 2-5 microns; the cumulative dissolution percentage was less than 20% within 60 min (FIG. 6).

COMPARATIVE EXAMPLE 7

In this comparative example, a solid dispersion of DQ was prepared by a HME method from a composition for HME comprising DQ as an active ingredient, Soluplus and Kollidon VA 64. The composition for HME comprised, by percentage of the total composition weight, 10% of DQ, 60% of Soluplus, and 30% of Kollidon VA 64. The specific preparation procedure was as follows:

| Decoquinate | 3 g |
|---|---|
| Soluplus | 18 g |
| Kollidon VA 64 | 9 g |

The above weighed materials were blended to homogeneity. The melting temperature of the twin-screw hot-melt extruder was set to 120-240° C., and the other steps were the same as in Example 1.

HPLC analysis showed that neither the retention time nor the content of DQ in the product was changed compared with the DQ standard; the particle size measurement showed that the average particle size of the DQ was 2-5 microns; and the cumulative dissolution percentage was less than 20% within 60 min (FIG. 7).

COMPARATIVE EXAMPLE 8

In this comparative example, a solid dispersion of DQ was prepared by a HME method from a composition for HME comprising DQ as an active ingredient, Soluplus and Kollidon VA 64. The composition for HME comprised, by percentage of the total composition weight, 20% of DQ, 71% of Soluplus, and 9% of Kollidon VA 64. The specific preparation procedure was as follows:

| Decoquinate | 6.0 g |
|---|---|
| Soluplus | 21.3 g |
| Kollidon VA 64 | 2.7 g |

The above weighed materials were blended to homogeneity. The melting temperature of the twin-screw hot-melt extruder was set to 120-240° C., and the other steps were the same as in Example 1.

HPLC analysis showed that neither the retention time nor the content of DQ in the product was changed compared with the DQ standard; the particle size measurement showed that the average particle size of the DQ was 2-5 microns; and the cumulative dissolution percentage was less than 20% within 60 min (FIG. 8).

The physicochemical properties and the biological effects of the products prepared in the above Examples and Comparative Examples were experimentally tested and the results analyzed were as follows:

Thermogravimetric Analysis

The pure DQ was weighed for thermogravimetric analysis. The instruments used in the analysis included a balance with 0.0001 accuracy (Sartorius, available from Sartorius Scientific Instruments, Model: BSA124S) and a thermogravimetric analyzer (NETZSCH, Model: TG209F1, Germany).

Detection conditions, nitrogen: 20 mL/min, scanning procedures: temperature was increased to 350° C. from room temperature, heating rate: 10° C./min; detection was performed based on the General Rules for Thermal Analysis JY/T014-1996. The thermogravimetric analysis of DQ showed that the amount of DQ was reduced to 99% by weight at 250.5° C., indicating that the compound was very stable, no thermal decomposition occurred and the minimal loss could be counted as water molecules. Thermogravimetric analysis of Soluplus, VA 64 and PEG 6000 also showed that these polymer carriers used for HME possess thermal stability.

Figure 9A:
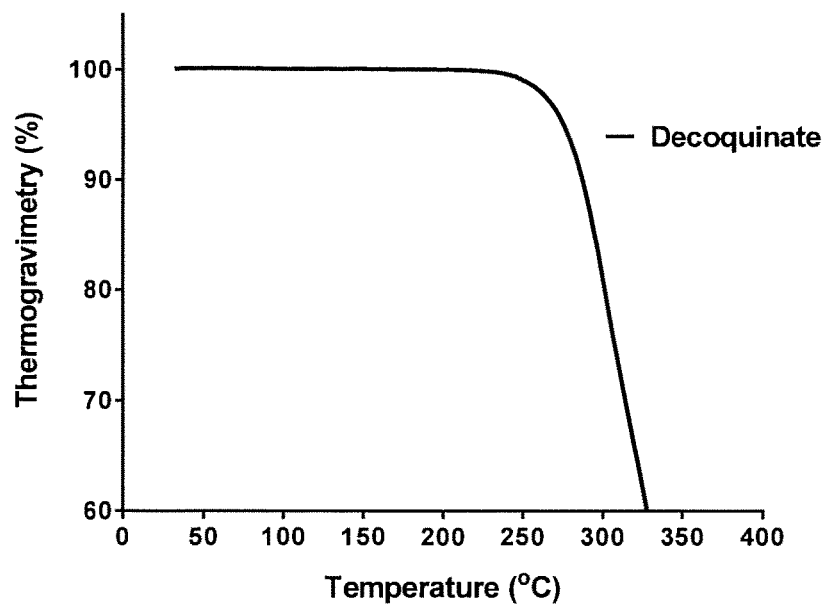
FIG. 9A is a thermogravimetric (TG) analysis graph of pure DQ.
Figure 9B:
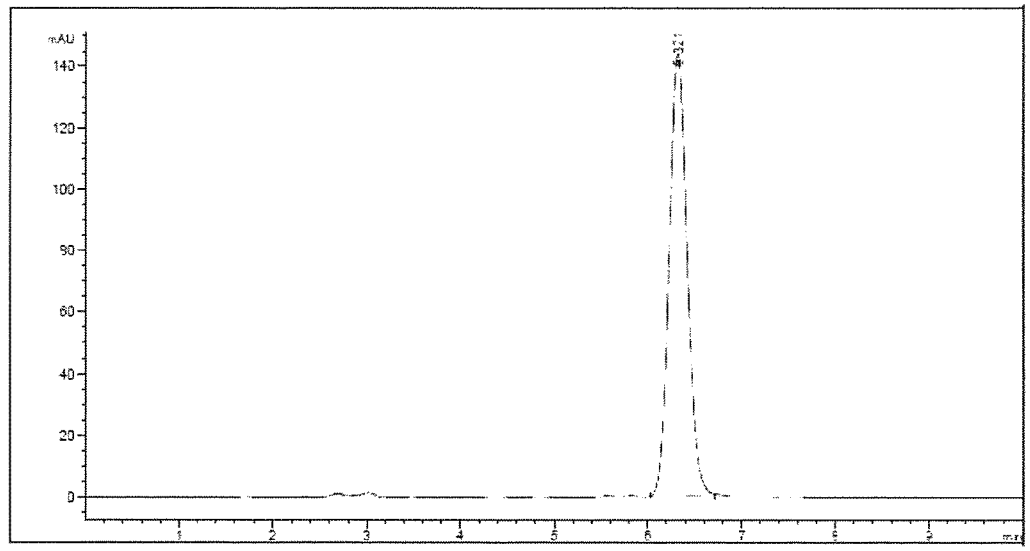
FIG. 9B is a High Pressure Liquid Chromatographic (HPLC) analysis graph of DQ in the solid dispersion of DQ prepared in Example 1.

FIG. 9A shows the thermogravimetric analysis graph of pure DQ. As can be seen from FIG. 9A, the amount of DQ was reduced to 99% by weight at 250.5° C., indicating that the compound was still very stable at this temperature and no thermal decomposition occurred. FIG. 9B is a high pressure liquid chromatographic analysis of DQ in the solid dispersion of DQ prepared in Example 1, which shows that neither the peak pattern nor retention time of DQ in the obtained product was changed, consistent with the results of the HPLC analysis of the product of Example 3 shown in FIG. 13, indicating that the active ingredient DQ in the hot-melt extruded product of the present invention did not undergo thermal decomposition.

Differential Scanning Calorimetry (DSC) Analysis

The hot-melt extruded products of DQ prepared in various examples were weighed and determined by DSC respectively. The reference materials included pure DQ, hot-melt extrudate only with formulation excipients, and a physical mixture of DQ and formulation excipients at room temperature. The instruments used in the analysis included a balance with 0.0001 accuracy (Sartorius, available from Sartorius Scientific Instruments, model: BSA124S) and a differential scanning calorimeter (DSC 204F1, NETZSCH, Germany).

The application method was $N_2$: 20 mL/min, the scanning program: accelerating the temperature from room temperature up to 265° C. at a rate of 10° C./min; the detection was carried out by following General Rules for Thermal Analysis JY/T014-1996.

Figure 10:
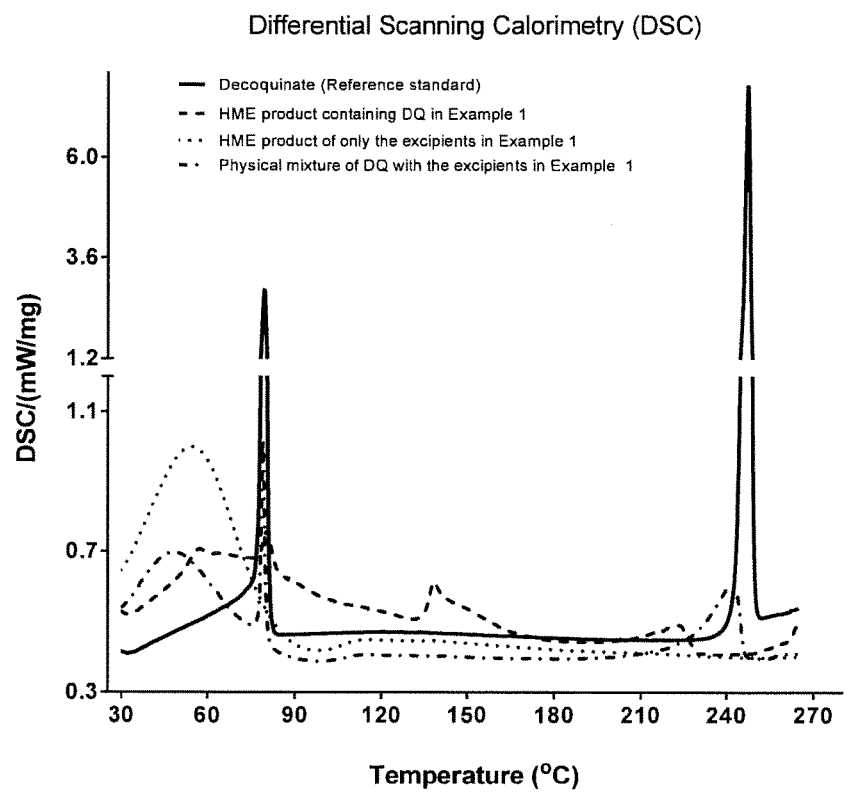
FIG. 10 is a Differential Scanning Calorimetry (DSC) graph of pure DQ, the hot-melt extrudate containing DQ prepared in Example 1, the hot melt extrudate of the ingredients other than DQ in Example 1, and physical mixture of DQ with excipients at room temperature.

Shown here only was the comparison of the DSC analysis graphs of pure DQ, the hot melt extrudate containing DQ prepared in Example 1, the hot melt extrudate of the components other than DQ in Example 1 and the physical mixture of DQ with excipients in Example 1 at room temperature (See FIG. 10). FIG. 10 shows that, in the solid dispersion of DQ prepared in Example 1, DQ and other polymer carriers were melted together; and the hot melt extrudate of DQ-free excipients did not have a typical peak pattern of pure DQ. In addition, when the DSC analysis was performed for the physical mixture of DQ and excipients, which were mixed together at room temperature, the mixture had an overlapping peak with pure DQ at a temperature below 90° C., and essentially no overlap at 240° C. or higher, which may be due to the melt of DQ with excipients to a certain extent as the temperature was increased during DSC analysis.

In Vitro Dissolution Test

The dissolution medium was a solution of 0.1 N hydrochloric acid (HCl) and 10 mM sodium dodecyl sulfonate (SDS). The instrument used in the test was RC-6 dissolution rate apparatus (Tianjin). The instrument parameters were set to 37° C., 50 rpm, the paddle method. To each dissolution vessel was added 900 ml of dissolution medium followed by initiating the instrument. When the temperature of the medium in each vessel reached 37° C., corresponding testing sample was added. One ml of sample solution was taken out at time points of 10, 20, 40, 60, 90, 120, 180, 240 and 270 minute respectively, and then 1 ml of dissolution medium was added back to supplement the vessel volume. The sample solutions collected from dissolution testing was passed through a 0.45 μm filter and the filtrate was analyzed by HPLC (Agilent, 1260) to determine the amount of DQ. An isocratic mobile phase of 80% ethanol and 20% water and a wavelength 260 nm were chosen for HPLC analysis.

Table 1 summarizes the percentage of each component in the ratio, melting temperature (™) and cumulative in vitro dissolution rate in the examples and comparative examples; wherein S: Soluplus; VA 64: copovidone Kollidon VA 64; PVP 10: polyvinylpyrrolidone-10; SDS: sodium dodecyl sulfonate; and PEG 6000: polyethylene glycol 6000.

TABLE 1

|  | Decoquinate | Soluplus | VA64 | PEG6000 | SDS | PVP 10 | TM (° C.) | Dissolved at 60 min | Dissolved at 90 min |
|---|---|---|---|---|---|---|---|---|---|
| Examples |  |  |  |  |  |  |  |  |  |
| 1 | 10 | 53 | 27 | 10 |  |  | 160 | 51.32 | 75.56 |
| 2 | 10 | 65 | 15 |  | 10 |  | 160 | 92.72 | 97.80 |
| 3 | 20 | 62.33 | 17.66 |  |  |  | 160 | 78.61 | 98.16 |
| 4 | 20 | 53 | 27 |  |  |  | 160 | 85.75 | 93.36 |
| 5 | 10 |  |  |  |  | 90 | 160 | 84.00 | 97.34 |
| 6 | 10 | 15 | 65 |  | 10 |  | 160 | 60.25 | 75.98 |
| 7 | 10 | 60 | 30 |  |  |  | 200 | 77.35 | 79.73 |
| 8 | 20 | 71 | 9 |  |  |  | 160 | 62.62 | 83.91 |
| Comparative Examples (below) |  |  |  |  |  |  |  |  |  |
| 1 | 10 | 60 | 30 |  |  |  | 160 | 84.76 | 87.50 |
| 2 | 10 | 70 | 20 |  |  |  | 160 | 16.00 | 39.00 |
| 3 | 20 | 62.33 | 17.66 |  |  |  | 160 | 2.14 | 3.42 |
| 4 | 20 | 53 | 27 |  |  |  | 160 | 1.50 | 20.70 |
| 5 | 10 | 90 |  |  |  |  | 160 | 5.94 | 26.25 |
| 6 | 10 | 20 | 70 |  |  |  | 160 | 5.89 | 22.13 |
| 7 | 10 | 60 | 30 |  |  |  | 240 | 10.59 | 24.36 |
| 8 | 20 | 71 | 9 |  |  |  | 240 | 3.90 | 10.84 |
| Pure DQ | 100 |  |  |  |  |  | 200 | 6.87 | 14.60 |

FIGS. 1 to 8 are graphs that showing comparative in vitro dissolution results of DQ in the solid dispersions of DQ prepared in Examples 1 to 8, DQ prepared in Comparative Examples 1 to 8 and pure DQ.

As seen from the results of FIGS. 1 to 8 and Table 1, compared with the solid dispersions of DQ prepared in the Comparative Examples (except Comparative Example 1) and pure DQ, the solid dispersions of DQ produced in the Examples of the present invention have significantly better in vitro dissolution. Although the solid dispersion of DQ prepared in Comparative Example 1 showed a better dissolution in vitro, the in vivo pharmacokinetics thereof is significantly inferior to that of the solid dispersion of DQ of Example 1 (see the pharmacokinetic experiments and experimental results thereof described below, FIG. 14).

Pharmacokinetic Experiments

The DQ standard curve for pharmacokinetic experiments was made by dissolving DQ in ethanol at a concentration of 0.1 mg/ml and then diluting it with ethanol to a series of concentrations (0.03 µg/ml to 30 µg/ml) to obtain a total of eight gradient concentrations. To each 45 µl of blank plasma, 5 µl of DQ standard solution and 5 µl of loratadine at a concentration of 10 µg/ml as internal standard were added, upon vigorous vortex for 30 seconds to mix samples, to which 150 µl of ethanol as a protein precipitant was added. After 2-minute vortex, a high speed centrifugation at 15,000 rpm for 5 min was performed under 4° C. Subsequently, 100 µl of the supernatant was taken and placed into the autosampler tube and a HPLC-MS/MS analysis was performed with 5 µl of an injection volume. The sample for quality control was decoquinate at 10, 300, and 2400 ng/ml, and the method for treatment was as described above. The chromatographic column was XTerra MS C18 5 µm, 4.6 mm×50 mm; Part No. 186000482; S/N: 03083432513203. The mobile phase consisted of 0.1% formic acid in methanol: 0.1% formic acid in water (90:10: v/v) at a flow rate of 600 µl/min. The column temperature was 30° C. and the temperature of injector 15° C.

The animals used in the pharmacokinetic studies of the present invention were male rats (sprague-dawley male rats). These rats were weighed prior to dosing, and their weights were generally between 180 to 200 grams. All rats were administrated at a dose of 20 mg/kg of DQ. The solid dispersion powder containing DQ was accurately weighed and dissolved in sterile saline solution with a brief ultrasound to prepare a suspension with a drug concentration of 2 mg/ml. Intragastric administration was performed with different volumes according to the weight of animals. The samples were collected with 250 µl of whole blood withdrawn from the tail vein at 15 minutes, 30 minutes, 1 hour, 2 hours, 4 hours, 6 hours, 8 hours, 24 hours, 48 hours and 72 hours after dosing the animals. Centrifugation was performed at 3500 rpm for 10 minutes at 4° C. in a centrifuge, and the supernatant plasma was taken and stored in a −80° C. refrigerator for further analysis. The plasma samples were treated by protein precipitation method. Ethanol was used as a protein precipitation reagent. Before analysis, the samples were treated by adding 5 µl loratadine standard solution (dissolved in ethanol) at a concentration of 10 µg/ml to 50 µl of plasma collected from dosed animals with test article, mixed by vigorous vortex for 30 seconds, and then 150 µl of ethanol was added to each sample as a protein precipitator. The remaining steps were the same as those of the preparation of the standard curve described above.

Table 2 shows the evaluation of the major pharmacokinetic parameters of the solid dispersions of DQ prepared in Example 1 and Comparative Example 1.

TABLE 2

| Pharmacokinetic parameters (mean) | PK parameters | Example 1 | Comparative Example 1 |
|---|---|---|---|
| Number of animals | n | 6 | 6 |
| Time point of maximal concentration (hour) | Tmax | 5.3 | 4 |
| Maximum concentration (ng/ml) | Cmax | 421.3 | 219 |
| Half-life (hours) | T½ | 81.2 | 36.1 |
| Area under the curve (hr*ng/ml) | AUClast (hr*ng/ml) | 15192.0 | 5078.4 |
| Area under the curve (hr*ng/ml) | AUCINF (hr*ng/ml) | 40384.3 | 8159.7 |

Figure 14:
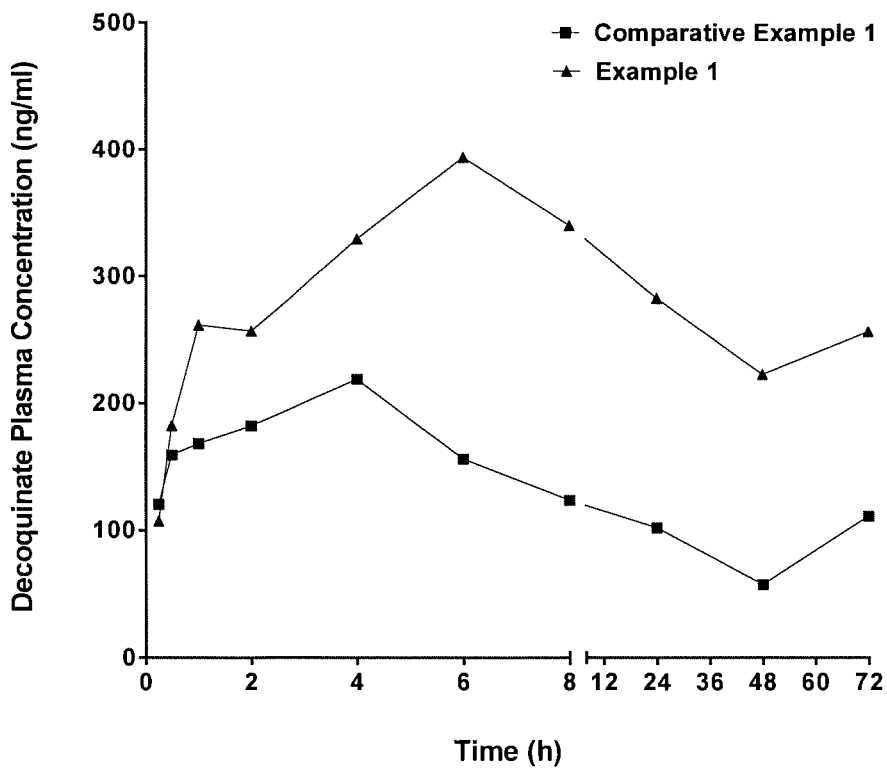
FIG. 14 illustrates pharmacokinetics of Example 1 and Comparative Example 1; wherein the ordinate represents the concentration of DQ in blood plasma and the abscissa represents the time of animal blood sampling.

FIG. 14 is a graph showing the pharmacokinetic profiles of Example 1 and Comparative Example 1, wherein the ordinate indicates the concentration of DQ in blood plasma and the abscissa indicates the animal blood sampling time.

As seen from Table 2 and FIG. 14, although the in vitro dissolution rate of Example 1 is not more effective than that of Comparative Example 1, the plasma concentration at the same time point in the animal is nearly twice that of Comparative Example 1, and the half-life is more than twice longer than that of Comparative Example 1. In comparing formulation components of the two, the difference lies in that PEG 6000 is included in Example 1 but not in Comparative Example 1. In the design of the present inventors, the addition of polyethylene glycol in an appropriate amount not only prolongs the circulation time of the active ingredient DQ in the blood of the body and prolongs the half-life but also enhances the concentration of DQ in the blood of an animal body, which favors improved efficacy.

In Vivo Efficacy Experiment

The NIH female mice used for the experiment were raised at least for 7 days after arrival. At the start of experiment, the mice were 7 weeks old. Only one mouse was housed in each cage maintained in a room with a temperature range of 18 to 26° C., a relative humidity of 34% to 68% in a 12/12 h light-dark cycle. Food and water were provided ad libitum during quarantine and throughout the study. This experiment was carried out in strict accordance with the relevant animal testing regulations (Guide for the Care and Use of Laboratory Animals, NRC publication, 2011 edition). The DQ suspension used in the animal experiment was from the product of Example 1, prepared with saline and subjected to ultrasonic treatment for 5 minutes. Each animal experiment was repeated at least three times with a group of 5 each time, so that at least 15 mice were tested in each group. NIH female mice were inoculated with Plasmodium by an injection of 50,000 sporozoites of Plasmodium berghei ANKA (Pb 868 sporozoites) through the tail vein of each mouse. Various preparations of the compounds were administered to mice by PO (oral administration or manually intragastric method) the day before, the day at and the day next to the Plasmodium inoculation. The positive control was primaquine, an antimalarial drug used for the liver-stage Plasmodium. Vehicle control was the components used in the solid dispersion of DQ other than DQ. No anti-malarial activity was found with the vehicle control, the results of which were consistent with those obtained by using only saline as a negative control. The detection of Plasmodium parasitemia was performed as follows: conventional method was used to count red blood cells per mm$^3$ of blood in that a thin film of blood was prepared and stained with 3% Giemsa for 20 minutes; and then the number of infected red blood cells per 1000 red blood cells was counted under oil microscope to obtain erythrocyte infected rate (EIR, ‰). Survival rate was calculated on day 22 post-infection.

Figure 15:
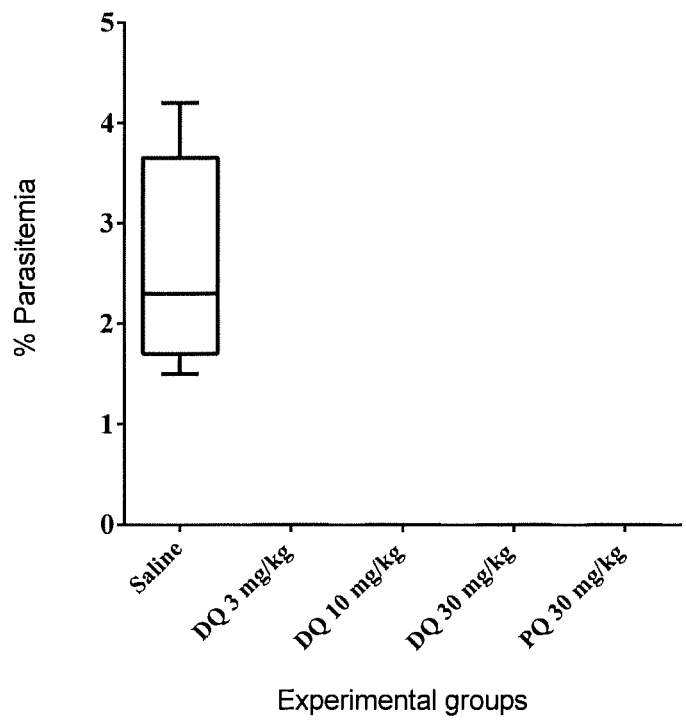
FIG. 15 illustrates animal efficacy test of the product prepared in Example 1; wherein DQ represents a group of the solid dispersion of DQ prepared in Example 1 at a dose of DQ per kg body weight; the saline group is used as a negative control; PQ represents the primaquine group, which is used as a positive control at a dose of 30 mg primaquine per kg body weight; the ordinate represents the percentage of parasitemia rate of *Plasmodium* in animal blood, the abscissa represents the experimental groups, and the figure shows a result on day 7 after *Plasmodium* inoculation.
Figure 16:
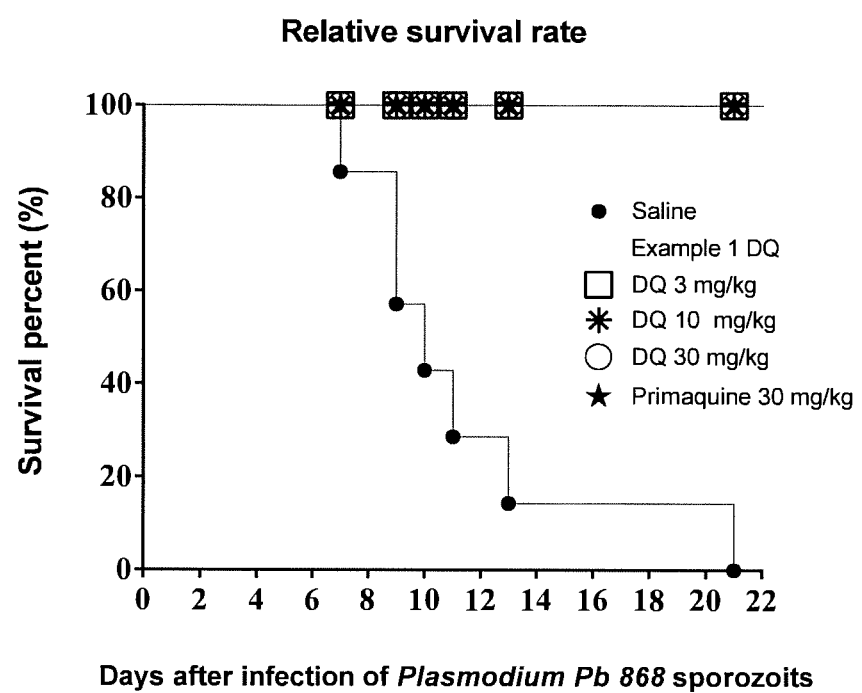
FIG. 16 illustrates a statistic of animal survival rate in a subsequently continuous experiment of the animal efficacy test of the product of Example 1 shown in FIG. 15.

FIG. 15 shows animal efficacy test of the product prepared in Example 1. The dosage of product of Example 1 was calculated based on decoquinate mg/kg body weight, the negative control group used was saline, and the positive control group used 30 mg primaquine per kg body weight. The ordinate indicates the blood stage parasitemia of the mice infected with Plasmodium, and the abscissa indicates the experimental groups. The results shown in the figure were of the 7th day after the infection of Plasmodium. FIG. 16 is a statistic of animal survival rate in a continuous experiment of the animal efficacy test of the product of Example 1 shown in FIG. 15.

As seen from FIGS. 15 and 16, after the formulation of Example 1 DQ was administered to mice at a dose of 3 mg/kg, 10 mg/kg, and 30 mg/kg, respectively, *Plasmodium* parasites were not detected in the blood, indicating that these three doses can effectively prevent the mice from the infection of *Plasmodium* sporozoites. In addition, it was observed that after 21 days, all animals survived when administered with the solid dispersion of DQ of the present invention or primaquine, whereas all animals in the control group died when no antimalarial administered.

The applicant declares that the present application illustrates the product, the application and the mode of the application of the present invention by above-described examples, but the present invention is not limited to the above-described detailed applications and the mode of the application, that is, it does not mean that the present invention must be carried out by relying upon the above-described detailed applications and the mode of the application. Those skilled in the pharmaceutical industry field should be aware that any modification of the invention, equivalents of the ingredients of the product of the invention, the addition of auxiliary ingredients, selection of specific modes, and the like are within the protection scope and the scope of disclosure of the present invention.

What is claimed is:

1. A preparation process of a solid dispersion of decoquinate, comprising the steps of combining decoquinate with solubilizing agent, plasticizer and excipient to form a molten composition; processing said composition in a twin-screw extruder with multiple reaction zones for pharmaceutical hot melt extrusion while heating at a melt temperature less than the degradation temperature of decoquinate; and extruding said composition to form an extrudate wherein said decoquinate in said extrudate is in an amorphous state.

2. The preparation process of claim 1, wherein said solubilizing agent is selected from the group consisting of polyvinyl caprolactam-polyvinyl acetate-polyethylene glycol graft copolymer, vinylpyrrolidone-vinylacetate copolymer and combinations thereof.

3. The preparation process of claim 1, wherein said solubilizing agent is present in an amount of at least 60% by weight in said composition.

4. The preparation process of claim 1, wherein said plasticizer is selected from the group consisting of polyoxyethylene hydrogenated castor oil, polyethylene glycol 2000-8000, and combinations thereof.

5. A preparation process of a solid dispersion of decoquinate, comprising the steps of combining decoquinate with solubilizing agent, excipient, and optionally plasticizer to form a molten composition, wherein said plasticizer is present in said composition in an amount of from about 0% to about 10% by weight of the composition; processing said composition in a twin-screw extruder with multiple reaction zones for pharmaceutical hot melt extrusion while heating at a melt temperature less than the degradation temperature of decoquinate; and extruding said composition to form an extrudate wherein said decoquinate in said extrudate is in an amorphous state.

6. The preparation process of claim 1, wherein the hot melt temperature is 50 to 200° C.

7. The preparation process of claim 1, wherein the hot melt temperature is 120 to 200° C.

8. The preparation process of claim 1, wherein the hot melt extruding is carried out in a hot melt extruder at a screw rotation speed range of 15 to 300 rpm.

9. The preparation process of claim 1, wherein the hot melt extruding is carried out in a hot melt extruder at a screw rotation speed range of 20 to 150 rpm.

10. The preparation process of claim 1, further comprising a step of compressing said extrudate to form a solid oral dosage form.

11. A method of treating a disease caused by *Plasmodium* parasite in a subject, comprising the administration of a therapeutically effective amount of the solid oral dosage form obtained from the preparation process of claim 10 to the subject.

12. The method of claim 11, wherein the disease is caused by any one or more of *Plasmodium vivax, Plasmodium falciparum, Plasmodium quartan, Plasmodium ovale* and *Plasmodium knowlesi.*

* * * * *